United States Patent
Eckstein et al.

(10) Patent No.: US 8,673,992 B2
(45) Date of Patent: Mar. 18, 2014

(54) POLYURETHANE GEL FOAMS

(75) Inventors: Axel Eckstein, Heidenheim (DE); Christian Schneider, Guegglingen (DE)

(73) Assignee: Paul Hartmann AG, Heidenheim (DE)

( * ) Notice: Subject to any disclaimer, the term of this patent is extended or adjusted under 35 U.S.C. 154(b) by 39 days.

(21) Appl. No.: 12/998,431

(22) PCT Filed: Oct. 21, 2009

(86) PCT No.: PCT/EP2009/007525
§ 371 (c)(1),
(2), (4) Date: Apr. 20, 2011

(87) PCT Pub. No.: WO2010/046095
PCT Pub. Date: Apr. 29, 2010

(65) Prior Publication Data
US 2011/0196329 A1    Aug. 11, 2011

(30) Foreign Application Priority Data
Oct. 23, 2008  (EP) .................................. 08018548

(51) Int. Cl.
*C08L 75/00* (2006.01)
*C08G 18/00* (2006.01)

(52) U.S. Cl.
USPC ............ 521/170; 521/137; 521/155; 521/174

(58) Field of Classification Search
USPC ......................................... 521/155, 170, 174
See application file for complete search history.

(56) References Cited

U.S. PATENT DOCUMENTS

| 4,520,139 A | * | 5/1985 | Kennedy | .................... 521/109.1 |
| 5,914,125 A | | 6/1999 | Andrews | |
| 6,509,388 B1 | * | 1/2003 | Addison | ........................ 521/159 |
| 2008/0293906 A1 | * | 11/2008 | Masters et al. | ................. 527/301 |

FOREIGN PATENT DOCUMENTS

| EP | 0 169 580 | | 1/1986 |
| JP | 2000-167036 | | 6/2000 |
| JP | 2008006401 A | * | 1/2008 |
| WO | 99/52569 | | 10/1999 |
| WO | WO 00/47241 | | 8/2000 |

OTHER PUBLICATIONS

Machine translation and English-language abstract of JP-2008006401-A.*
English-language abstract and machine translation of JP 2008006401-A accessed on the Japan Patent Office website on Sep. 24, 2012.*

* cited by examiner

*Primary Examiner* — Melissa Rioja
(74) *Attorney, Agent, or Firm* — Paul Vincent (57) ABSTRACT

Polyurethane gel foams are proposed as is their use in modern wound treatment. In particular, wound dressings comprise polyurethane gel foams for treating moderately to severely exuding wounds. The polyurethane gel foams are thereby produced from an isocyanate component A having a functionality f of $f_A \leq 3$, a polymeric polyol component B having a functionality f of $f_B \leq 6$, and a polysaccharide C, comprising at least one uronic acid or a salt thereof, wherein the ratio of the number of isocyanates groups of the isocyananate component A to the total number of hydroxyl groups, carboxy groups and carboxylate groups in the polymeric polyol component B and the polysaccharide C corresponds to the ratio 1:2 to 1:30.

8 Claims, 3 Drawing Sheets

POLYURETHANE GEL FOAMS

This application is the national stage of PCT/EP2009/007525 filed on Oct. 21,2009 and claims Paris Convention Priority to EP 08 018 548.1 filed Oct. 23, 2008.

BACKGROUND OF THE INVENTION

The present invention relates to polyurethane gel foams and to the use thereof in modern wound treatment. In particular, the present invention relates to wound dressings comprising polyurethane gel foams for treating moderately to severely exuding wounds.

Polyurethane gel foams have been known for some time. For example, international application WO 88/01878 A1 describes self-adhesive polyurethane foams or polyurethane gel foams. These polyurethane gel foams are used as the wound contact layer in wound dressings.

Furthermore, hydrophilic foams made of polyurethane gel are described in the international applications WO 92/17518 A1 and WO 94/07935 A1. These foams are manufactured from at least one polyether polyol, at least one diisocyanate, water, accelerator and one or more superabsorbent polymers, wherein the components are mixed and possibly foamed by adding gases.

Moreover, international application WO 97/43328 A1 describes a self-adhesive polyurethane gel or polyurethane foam gel that is manufactured from an aliphatic diisocyanate, a polyol component, a stabilizer and reaction accelerators. These polyurethane foam gels do not contain a proportion of polysaccharides.

From U.S. Pat. No. 5,833,665 A, a dressing for fixing a catheter is known. The wound dressing comprises pillow wound dressing made of an isocyanate prepolymer and a biopolymer, which releases medication. The biopolymer might be, for example, pectin, gelatine, or algin.

Furthermore, international patent application WO 00/47241 A1 describes a polyurethane foam for use as a wound contact layer that is manufactured from an isocyanate component or an isocyanate prepolymer, water and alginic acid or a salt thereof. If necessary, a monohydric $C_1$-$C_3$ alcohol can be added to the reaction mixture. Because of the incorporation of alginic acid, this polyurethane foam exhibits an improved absorption capability.

In WO 01/62818 A1 it is suggested that, to manufacture a polyurethane pressure-sensitive adhesive, two polyols or any other materials that react with NCO groups be obtained from isocyanates, wherein the components reacting with the isocyanates differ from each other in that the first polyol component has a molar mass greater than 2000 and the second polyol component has a molar mass less than 2000.

Furthermore, European patent application EP 1923077 A1 describes a multiple-layer dressing having a wound contact layer made of a hydrophilic, self-adhesive polyurethane elastomer. The elastomer is manufactured from a diisocyanate prepolymer and a polymer polyhydroxyl component.

Overall, it can be ascertained here that the proposed polyurethane gel foams exhibit a permeability that is at least partially insufficient for wound exudate.

Based on the prior art, the object of this invention is to provide alternative and improved polyurethane gel foams and wound dressings manufactured therefrom for treating secreting wounds. In particular, the polyurethane gel foams should be suitable for use as a wound contact layer in modern wound management. A wound dressing manufactured with this polyurethane gel foam should further not have wound adhering properties and should also prevent maceration of the skin surrounding the wound.

SUMMARY OF THE INVENTION

This object is achieved in a surprising manner by a polyurethane gel foam according to the independent claim. An inventive polyurethane gel foam for use as a wound contact layer is thereby derived from at least the following components, which are made to react:
    a) an isocyanate component A having a functionality f of $f_A \leq 3$,
    b) a polymeric polyol component B having a functionality f of $f_B \leq 6$, and
    c) a polysaccharide C, comprising at least one uronic acid or a salt thereof,
wherein the ratio of the number of isocyanate groups of the isocyanate component A to the total number of hydroxyl groups, carboxy groups and carboxylate groups in the polymeric polyol component B and in the polysaccharide C corresponds to the ratio 1:2 to 1:30.

Independently of this, a dressing comprising a polyurethane gel foam, in particular as a wound contact layer, is the object of this invention. This polyurethane gel foam is obtained from at least the following components, which are made to react:
    a) an isocyanate component A having a functionality f of $f_A \leq 3$,
    b) a polymeric polyol component B having a functionality f of $f_B \leq 6$, and
    c) a polysaccharide C, comprising at least one uronic acid or a salt thereof,
wherein the ratio of the number of isocyanate groups of the isocyanate component A to the total number of hydroxyl groups, carboxy groups and carboxylate groups in the polymeric polyol component B and in the polysaccharide C corresponds to the ratio 1:2 to 1:30.

According to a further embodiment of this invention, the ratio of the number of isocyanate groups of the isocyanate component A to the total number of hydroxyl groups, carboxy groups and carboxylate groups in polymeric polyol component B and in polysaccharide C corresponds to the ratio 1:3 to 1:30, in particular 1:4 to 1:30, in particular 1:4 to 1:20, and highly preferably 1:5 to 1:20.

It must be emphasized here that both the polymeric polyol component B and polysaccharide C are reactants that react with the isocyanate component A. Herein, polysaccharide C can react with the isocyanate component A, by means of the existing hydroxyl groups, thus forming a urethane bond, and by means of an existing carboxy group of the uronic acid, thus forming an amide bond. This amide bond is formed with simultaneous release of gaseous carbon dioxide, wherein the polyurethane gel foam is produced without introducing additional gases.

The polyurethane gel foam produced in this way is particularly kind to the skin and does not cause irritation on a wound or the skin surrounding the wound when it makes direct contact with the body. By using the polysaccharide with at least one uronic acid, a polyurethane gel foam can be provided with a novel polymer structure that exhibits improved permeation kinetics.

A special advantage of the wound dressing comprising this polyurethane gel foam is that, by using the polyurethane gel foam as a wound contact layer, a spacer layer between an absorbent layer and a wound is created and thus any other materials that tend to adhere to the wound can be used as the absorbent layer. Moreover, a wound contact layer that does not adhere to the wound is created by means of the polyurethane gel foam, which permits improved transfer of wound exudate from the wound to an absorbent layer because of its foam properties. In addition, it has been shown that this dressing prevents or at least reduces maceration, that is, the softening and attendant damage of the skin surrounding the wound. As a result, a dressing can be provided that protects the skin surrounding the wound and that promotes wound healing to a large extent.

In particular, to obtain the inventive polyurethane gel foams, besides the specified components, no water is made to react with the exception of the residual water content in the components. Thus, a polyurethane gel foam or a wound dressing comprising this polyurethane gel foam is the object of the invention and is obtained from the following components, which are made to react:

a) an isocyanate component A having a functionality f of $f_A \leq 3$,
b) a polymeric polyol component B having a functionality f of $f_B \leq 6$, and
c) a polysaccharide C, comprising at least one uronic acid or a salt thereof, wherein the reaction is performed without the addition of water and the ratio of the number of isocyanate groups of the isocyanate component A to the total number of hydroxyl groups, carboxy groups and carboxylate groups in the polymeric polyol component B and in the polysaccharide C corresponds to the ratio 1:2 to 1:30.

An anhydrous polyurethane gel foam is therefore also the object of this invention. In the context of this invention, an anhydrous polyurethane gel foam or any anhydrous compound or component means a polyurethane gel foam, compound or component that contains less than 4% by weight of water relative to the weight of the polyurethane gel foam or the relevant compound or component. In particular, such a polyurethane gel foam or such a compound or component contains less than 2% by weight of water, preferably less than 1% by weight of water and highly preferably less than 0.5% by weight of water.

In addition or alternatively, according to a further embodiment of this invention, the ratio of the number of isocyanate groups of isocyanate component A to the total number of carboxyl groups and carboxylate groups in polysaccharide C corresponds to the ratio 1:0.5 to 1:10. In particular, the ratio of the number of isocyanate groups of isocyanate component A to the total number of carboxy groups and carboxylate groups in polysaccharide C can be set from 1:1 to 1:10, preferably 1:2 to 1:10 and highly preferably from 1:3 to 1:10. In this way, a polyurethane foam can be provided that exhibits a particularly even foam structure.

According to this invention, inventive polyurethane gel foams are obtained using isocyanate components A with a functionality $f_A$, where $f_A \leq 3$. In a first aspect of the invention, these include isocyanate components that exhibit a maximum of three isocyanate groups in an idealized formula scheme. According to this invention, this number of reactive groups must be used to determine the ratios of the components to be used. The average functionality $\bar{f}_A$ that actually exists of an isocyanate component A used can deviate from this functionality $f_A$.

Furthermore, according to a further aspect of this invention, isocyanate component A is understood to be those isocyanates of aliphatic, alicyclic, heterocyclic, aromatic, and heteroaromatic origin having a functionality f of $f_A \leq 3$, i.e. ideally have no more than 3 isocyanate groups. According to a further aspect, this also includes those isocyanates that are termed isocyanate prepolymers manufactured from an aliphatic, alicyclic, heterocyclic, aromatic or heteroaromatic di- or polyisocyanate and a polyol, and having a functionality f of $f_A \leq 3$.

According to a preferred embodiment of this invention, in particular those isocyanates, in particular, aliphatic or alicyclic isocyanates, can be used as isocyanate component A that have a functionality f of $1 \leq f_A \leq 3$. Isocyanates that exhibit a functionality f of $2 \leq f_A \leq 3$ are especially preferred.

According to this invention, aliphatic or alicyclic di- or polyisocyanates and/or di- or polyisocyanates with non-aromatic linked isocyanate groups can be used to create polyurethane gel foams of adequate stability. Surprisingly it was found that aliphatic or alicyclic di- or polyisocyanates are suitable for additionally producing the equally desirable property profile of polyurethane gel foams according to the object of the invention. It must be particularly emphasized that the surface-specific selectivity of the pressure-sensitive adhesive properties can be achieved particularly well when aliphatic or alicyclic di- or polyisocyanates are used.

Examples of suitable, inventive di- or polyisocyanates are the aromatic diisocyanates MDI (methylene diphenyl diisocyanate), TDI (toluene diisocyanate), XDI (xylylene diisocyanate), NDI (naphthalene diisocyanate) or phenylene diisocyanate. In particular, however, dicyclohexylmethane diisocyanate, butane-1,4-diisocyanate, tetramethoxy butane-1,4-diisocyanate, hexane-1,6-diisocyanate, ethylene diisocyanate, 2,2,4-trimethyl hexamethylene diisocyanate, ethylethylene diisocyanate, dicyclohexyl methane diisocyanate, 1,4-diisocyanatocyclohexane, 1,3-diisocyanatocyclohexane, 1,2-diisocyanatocyclohexane, 1,3-diisocyanatocyclopentane, 1,2-diisocyanatocyclopentane, 1,2-diisocyanatocyclobutane, 1-isocyanatomethyl-3-isocyanato-1,5,5-trimethylcyclohexane (isophorone diisocyanate, IPDI), 1-methyl-2,4-diisocyanatocyclohexane, 1,6-diisocyanato-2,2,4-trimethylhexane, 1,6-diisocyanato-2,4,4-trimethylhexane, 5-isocyanato-1-(2-isocyanatoeth-1-yl)-1,3,3-trimethylcyclohexane, 5-isocyanato-1-(3-isocyanatoprop-1-yl)-1,3,3-trimethylcyclohexane, 5-isocyanato-1-(4-isocyanatobut-1-yl)-1,3,3-trimethylcyclohexane, 1-isocyanato-2-(3-isocyanatoprop-1-yl)-cyclohexane, 1-isocyanato-2-(2-isocyanatoeth-1-yl)-cyclohexane, 2-heptyl-3,4-to(9-isocyanatononyl)-1-pentylcyclohexane or norbornane diisocyanatomethyl are to be used as the aliphatic or alicyclic di- or polyisocyanates. However, chlorinated, bromated aliphatic or alicyclic di- or polyisocyanates or those containing sulfur or phosphor, as well as derivatives of the listed diisocyanates, in particular dimerized or trimerized types, can be used. In particular, uretdiones or isocyanurates of aliphatic or alicyclic di- or polysocyanates can be used according to the invention.

According to another embodiment of the invention, polyurethane gel foams that are made from aliphatic or alicyclic di- or polyisocyanates or mixtures thereof are preferred. In particular, linear aliphatic or alicyclic diisocyanates are preferred, wherein pentamer or hexamer alicyclic diisocyanates are further preferred. In an especially preferred embodiment, isophorone diisocyanate is used as a hexamer alicyclic diisocyanate, which permits very good permeation kinetics for wound exudate.

Further prepolymers are preferred as an isocyanate component that consist of alphatic or alicyclic di- or polyisocyanates and di- or polyols; further, prepolymers are preferred that consist of alicyclic diisocyanates, wherein, in particular, polyether polyols or polyester polyols are used as polyols.

Such isocyanate prepolymers are manufactured by reaction of higher molecular polyhydroxyl compounds (polyols), such as, for example, polyether or polyester polyols with excess quantities of di- or polyisocyanate. In this case, it is an advantage if the isocyanate groups exhibit different reactivities. This characteristic ensures that the unwanted monomer content is repressed. The products also exhibit low viscosities and better technical processing properties. For example, isophorone diisocyanate (3-isocyanatomethyl-3,5,5-trimethylcyclohexyl isocyanate, IPDI) contains two such differently (selectively) reactive isocyanate groups.

Therefore, according to a further preferred embodiment, those polyurethane gel foams are particularly preferred which are obtained when an isophorone diisocyanate prepolymer or a mixture thereof is used as the isocyanate component A isophorone diisocyanate, wherein the isophorone diisocyanate prepolymer can be obtained from isophorone diisocyanate and a polyether polyol D with functionality f of $f_D \le 3$.

In a highly preferred embodiment, polyurethane gel foams are used that are obtained when an isophorone diisocyanate prepolymer is used as the isocyanate component A, which can be obtained from isophorone diisocyanate and a polyether polyol D, wherein the polyether polyol D is selected from the group of polyethylene glycols, polypropylene glycols, polyethylene polypropylene glycols or mixtures of thereof, and wherein the polyether polyol D exhibits a mean number-average molar mass $M_n$ of at least $M_n (D)=2000$ g/mol and no more than $M_n (D)=10,000$ g/mol.

According to this invention, in particular, an isophorone diisocyanate prepolymer according to formula (I) can be made to react as the isocyanate component A.

(I)

Herein the following applies:

n, m are mutually independent: n, m=0 to 120, where n+m≠0.

In particular, according to this invention, those isocyanate prepolymers according to formula (I) are preferred for which n=0 and m=1 to 120. Those prepolymers where n=0 and m=30 to 120 are highly preferably used, especially preferably where n=0 and m=30 to 90, and highly preferably where n=0 and m=40 to 80.

According to a further embodiment of this invention, those prepolymers according to formula (I) can also be used for which n=1 to 120 and m=0. Those prepolymers where n=30 to 120 and m=0 are especially preferably used, especially preferably where n=30 to 90 and m=0, and highly preferably where n=40 to 80 and m=0.

As a rule, the isocyanate prepolymers that can be used as part of this invention, in particular diisocyanate prepolymers, have a mean number-average molar mass of approximately 500 g/mol to approximately 15,000 g/mol, preferably approximately 500 g/mol to approximately 10,000 g/mol, especially preferably approximately 1,000 g/mol to approximately 10,000 g/mol, especially preferably approximately 2,000 g/mol to approximately 10,000 g/mol and highly preferably 3,000 g/mol to approximately 10,000 g/mol.

According to this invention, inventive polyurethane gel foams are obtained when those polyol components are used as polymeric polyol component B that have a functionality f of $f_B \le 6$. Analogously to isocyanate component A, according to a first aspect, these include those polyol components that have no more than six hydroxyl groups in an idealized formula scheme. According to this invention, this number of reactive groups must be used to determine the ratios of the components to be used. The real mean functionality $\bar{f}_B$ of a polyol component used may deviate from this functionality $f_B$.

According to a preferred embodiment of this invention, those polyols, in particular polyether polyols, that have a functionality f of $3 \le f_B \le 6$ can preferably be used as the polyol component B. Polyether polyols that have a functionality f of $3 \le f_B \le 5$ are especially preferred. Polyether polyols that have a functionality f of $4 \le f_B \le 5$ are highly preferred.

Examples of suitable inventive dioles or polyols include oxyalkyl polymers, preferably polyether polyols with OH numbers between 20 and 112 bearing 2, 3, 4, 5 or 6 hydroxyl groups and an ethylene oxide content of ≥10% by weight, preferably 10 to 40% by weight, especially preferably 10 to 20° A) by weight, polyacryl polyols, polyester polyols, polyolefin polyols, polythiol polyols, polyamine compounds. The glass transition temperatures should be as low as possible, i.e. below approximately 20° C., preferably below approximately 0° C., especially preferably below approximately −10° C.

Polyether polyols with mean number-average molar masses $M_n$ (B) between 600 and 12,000 g/mol are preferred and can be obtained by the known methods and/or by reacting the initiator compounds with a reactive H atom with alkylene oxides (for example, ethylene and/or propylene oxide, preferably propylene oxide, butylene oxide, styrene oxide, tetrahydrofuran or epichlorhydrin or mixtures of two or more thereof). Tetramethylene ether glycol can also be used. Equally possible are additional modifications with, for example monoethylene glycol (MEG), dipropylene glycol (DPG), trimethylolpropane (TMP). Aliphatic polyether polyols are currently preferred for use in medicine.

Suitable initiator compounds include, for example, water, ethylene glycol, propylene glycol-1,2 or -1,3, butylene glycol-1,4 or -1,3, hexanediol-1,6, octanediol-1,8, pentanediol-1,5, heptanediol-1,7, and their higher homologs, neopentyl glycol, 1,4-hydroxymethyl cyclohexane, 2-methyl-1,3-propanediol, glycerine, trimethyloipropane, 2,2-(bis-4,4'-hydroxyphenyl)-propane, trimethyloipropane, glycerine or pentaerythritol, hexanetriol-1,2,6, butanetriol-1,2,4 trimethylolethane, mannitol, sorbitol, methylglucosides, sugar, phenol, isononylphenol, resorcin, hydrochinon, 1,2,2- or 1,1, 2-tris(hydroxyphenyl)ethane, ammonia, methylamine, ethylendiamine, tetra- or hexamethyleneamine, triethanolamine, aniline, phenylenediamine, 2,4- and 2,6-diaminotoluene and polyphenyl polymethylene polyamine, as they can be obtained from aniline formaldehyde condensation, or mixtures of the above initiator compounds.

In particular, polyether polyols are to be used as the polyol component B for producing the inventive polyurethane gel foams. Polyether polyols with a mean number-average molar mass $M_n$ (B) of 600 to 12,000 g/mol are especially preferred. In particular, however, polyether polyols can be used that have a mean number-average molar mass of $M_n$ (B) between 600 and 10,000 g/mol, especially between 1,000 and 10,000 g/mol, and highly preferably between 2,000 and 10,000 g/mol. It has further proven advantageous if polyether polyols are used that have a mean number-average molar mass $M_n$ (B) of between 3,000 and 10,000 g/mol.

Polyacrylates bearing OH groups are also equally suitable as diol or polyol components. These are obtained, for example, by the polymerization of ethylenically unsaturated monomers that bear an OH group. Such monomers can be obtained, for example, by the esterification of ethylenically unsaturated carboxylic acids and difunctional alcohols, wherein there is usually a slight excess of alcohol. Such unsaturated carboxylic acids are, for example, acrylic acid, methacrylic acid, crotonic acid or maleic acid. The relevant OH-group-bearing esters are, for example, 2-hydroxyethyl acrylate, 2-hydroxyethyl methacrylate, 2-hydroxypropyl acrylate, 2-hydroxypropyl methacrylate, 3-hydroxypropyl acrylate or 3-hydroxypropyl methacrylate or mixtures of two or more thereof.

Polyester polyols, in particular, with a mean number-average molar mass of approximately 200 to approximately 10,000 g/mol, are equally suitable as diol or polyol components. For example, polyester polyols can be used that are formed by the reaction of low-molecular alcohols, in particular, ethylene glycol, diethylene glycol, neopentyl glycol, hexandiol, butandiol, propylene glycol, glycerine or trimethylol propane with caprolactone. 1,4-hydroxy-methylcyclohexane, 2-methyl-1,3-propandiol, butantriol-1,2,4, triethylene glycol, tetraethylene glycol, polyethylene glycol, dipropylene glycol, polypropylene glycol, dibutylene glycol and polybutylene glycol are equally suitable as polyfunctional alcohols for the manufacture of polyester polyols. Further suitable polyester polyols can be manufactured by polycondensation. In this way, difunctional and/or trifunctional alcohols can be condensed to polyester polyols with a deficiency of dicarboxylic acids and/or tricarboxylic acids, or their reactive derivatives. Suitable dicarboxylic acids include, for example, adipic acid or succinic acid and their homologs with up to 16 C atoms, further, unsaturated dicarboxylic acids such as maleic acid or fumaric acid, as well as aromatic dicarboxylic acids, in particular, the phthalic acid isomers, such as phthalic acid, isophthalic acid or terephthalic acid. Suitable tricarboxylic acids are, for example, citric acid or trimellitic acid. The above-mentioned acids can be used individually or as mixtures of two or more thereof. Particularly suitable are polyester polyols made of at least one of the mentioned dicarboxylic acids and glycerine, which have a residual content of OH groups. Particularly suitable alcohols are hexandiol, ethelyne glycol, diethylene glycol or neopentyl glycol or mixtures of two or more thereof. Particularly suitable acids are isophthalic acid or adipic acid or mixtures thereof. Polyester polyols with a higher mean number-average molar mass $M_n$ particularly in the range of >5000 g/mol comprise, for example, the products of conversion of polyfunctional, preferably difunctional alcohols (possibly in combination with small quantities of trifunctional alcohols) and polyfunctional, preferably difunctional carboxylic acids. Instead of free polycarboxylic acids, it is also possible to use (if available) the corresponding polycarboxylic anhydrides or corresponding polycarboxylic esters with alcohols with preferably 1 to 3 C atoms. The polycarboxylic acids can be aliphatic, alicyclic, aromatic or heterocyclic polycarboxylic acids. They can be substituted, for example, by alkyl groups, alkenyl groups, ether groups or halogens.

Suitable polycarboxylic acids are, for example, succinic acid, adipic acid, suberic acid, azelaic acid, sebacic acid, phthalic acid, isophalic acid, terephthalic acid, trimellitic acid, phthalic anhydride, tetrahydrophthalic anhydride, hexahydrophthalic anhydride, tetrachlorphthalic anhydride, endomethylentetrahydrophthalic anhydride, glutaric anhydride, maleic acid, maleic anhydride, fumaric acid, dimer fatty acid or trimer fatty acid or mixtures of two or more thereof. Possible, minor quantities of monofunctional fatty acids may be present in the reaction mixture. The polyester may have a small proportion of carboxy end groups. Polyesters obtained from lactone, for example, epsilon-caprolactone or hydroxyl carboxylic acids, for example, omega-hydroxycaproic acid, can also be used.

The above-mentioned diols and polyols can also be mixed. In so doing, their compatibility must be observed. Aliphatic polyester polyols are preferably used in the context of this invention.

According to this invention, an inventive polyurethane gel foam is obtained in which at least one polysaccharide C that comprises at least one uronic acid is made to react with an isocyanate component A and a polyol component B. In the context of this invention, polysaccharide refers to a macromolecular compound that comprises at least ten monosaccharide molecules linked by a glycosidic bond. In this context, therefore, a polysaccharide that comprises at least one uronic acid or a salt thereof, is understood to be a polysaccharide that comprises at least nine monosaccharide molecules and one uronic acid molecule, wherein these components are linked by a glycosidic bond. Furthermore, a uronic acid is a monosaccharide, whose primary alcohol function (—CH$_2$OH) is oxidized to a carboxy function (—COOH). A uronic acid (aldehyde acid) has the following general formula (II).

$$O=CH-[CH(OH)]_n-COOH \text{ where } (n \geq 2) \qquad (II)$$

In particular, according to the invention, such uronic acids are used for which n=5 or 6. Thus, according to a further aspect of this invention, polysaccharides are preferably used which comprise at least one penturonic acid having the general formula (III) or one hexuronic acid having the general formula (IV).

(III)

(IV)

According to a further idea of this invention, in particular, polysaccharides C can be made to react that comprise, as the uronic acid, guluronic acid or a salt thereof, mannuronic acid or a salt thereof, galacturonic acid or a salt thereof, glucuronic acid or a salt thereof, iduronic acid or a salt thereof, or mixtures of these acids or salts thereof.

In particular, however, the polysaccharide C can be selected from the group of alginic acid or salts thereof, hyaluronic acid or salts thereof, glucose aminoglycans or salts thereof, the xanthans or salts thereof, or mixtures of these polysaccharides or salts thereof. These polysaccharides have differing quantities of uronic acid. For example, glycosaminoglycans exhibit bonded units of disaccharides as naturally occurring polysaccharides1-4, which comprise glucuronic acid or iduronic acid as the uronic acid.

Alginic acids or salts thereof can highly preferably be used as polysaccharides C. Alginic acid exhibits a structure that can be expressed by the general formula (V). Thus, alginic acid is essentially composed of (V)

mannuronic acid and guluronic acid.

Herein the following applies:

n, m are mutually independent: n, m=120 to 1000.

In particular, according to this invention, alginic acids according to formula (V) are preferred for which, mutually independently, n=200 and m=1,000 to 120 apply. Those alginic acids where, mutually independently n,m=200 to 1,000, highly preferably, n,m=400 to 1,000 and especially preferably n, m=600 to 1,000 are highly preferred.

Further, calcium alginates, sodium aginates, sodium calcium alginates or mixtures thereof can preferably be used as polysaccharides C. The trunk chain of these polysaccharides consists of almost 100% guluronic acid and mannuronic acid. Because of the high proportion of uronic acids, a polyurethane gel foam can be provided that is especially suitable for use as a wound contact layer. These polyurethane gel foams have a cell structure that especially favors the permeation of wound exudate.

As a rule, the polysaccharides C that can be used as part of this invention, in particular, the alginic acids or salts thereof that are used, have a mean number-average molar mass of approximately 2000 g/mol to approximately 300,000 g/mol, preferably approximately 5000 g/mol to approximately 300,000 g/mol, especially preferably approximately 10,000 g/mol to approximately 300,000 g/mol, especially preferably approximately 10,000 g/mol to approximately 250,000 g/mol and highly preferably 100,000 g/mol to approximately 250,000 g/mol.

If applicable, the inventive polyurethane gel foam can be produced by means of auxiliary and additional substances. According to this invention, in particular, catalysts, plasticizers, stabilizers, such as anti-oxidants or photostabilizers, tackifiers, colorants, fillers, thickening agents or rheological additives can be deployed as auxiliary and additional substances.

In particular, bismuth(III)-carboxylate based on linear, branched, saturated or unsaturated carboxylic acids with 2 to 18, preferably 6 to 18 C atoms can be used as catalysts for producing inventive polyurethane gel foams. Further preferred are Bi(III) salts of branched saturated carboxylic acids with tertiary carboxy groups, such as the 2,2-dimethyl-octanoic acid (e.g. Versatic acids, Shell Germany). Preparations of these bi(III) salts in excess proportions of these carboxylic acids are very suitable. A solution of 1 mol of the bi(III) salt of the Versatic 10 acid (2,2-dimethyloctanoic acid) in an excess of 3 mol of this acid with a bismuth content of approx. 17% has proven excellent. These catalysts can be presented, in particular, in the polymeric polyol component B. The catalysts are preferably used in quantities of 0.03 to 0.5% by weight relative to the polymeric polyol component B.

By way of example, phthalic acid derivatives are used as plasticizers, for example, phthalic acid ester, which has 6 to 12 carbon atoms and has been esterified with a linear alcanol, e.g. dioctyl phthalate. Polyethylene gycols and their derivates, vegetable and animal oils, such as glycerine esters of fatty acids and their polymerization products and benzoate compounds (benzoate plasticizers, for example, sucrose benzoate, diethylene glycol dibenzoate and/or diethylene glycol benzoate, in which approximately 50 to approximately 95% of all hydroxyl groups have been esterified, phosphate plasticizers, for example, t-butylphenyl diphenyl phosphate, polyethylene glycols and their derivatives, for example, diphenyl ethers of poly(ethylene glycol), liquid resin derivatives, for example, the methyl ester of hydrated resin are also suitable as plasticizers. Aliphatic diesters such as adipic or sebacic dinonyl esters are especially preferred.

The stabilizers (anti-oxidants) used as part of the invention include sterically inhibited phenols such as BHT (2,6-Di-tert-butyl-4-methylphenol), Irganox® 1010, 1076, 1330, 1520 (Ciba Speciality Chemicals) and tocopherols. Vitamin E (alpha-tocopherol) is especially preferably used. Polyfunctional phenols and compounds containing sulfur and phosphorus and/or 1,3,5-trimethyl-2,4,6-tris(3,5-di-tert-butyl-4-hydroxybenzyl)benzol; pentaerythritol-tetrakis-3-(3,5-di-tert-butyl-4-hydroxyphenyl)propionate; n-octadecyl-3,5-di-tert-butyl-4-hydroxyphenyl)propionate; 4,4-methylenbis(2,6-di-tert-butyl-phenol); 4,4-thiobis(6-tert-butyl-o-cresol); 2,6-di-tert-butylphenol; 6-(4-hydroxyphenoxy)-2,4-bis(n-octylthio)-1,3,5-triazine; di-n-octadecyl-3,5-di-tert-butyl-4-hydroxybenzyl-phos-phonate; 2-(n-octylthio)ethyl-3,5-di-tert-butyl-4-hydroxy-benzoate; and sorbithexa[3-(3,5-di-tertbutyl-4-hydroxy-phenyl)-propionate] can also be used. As photostabilizers, for example, Tinuvin® products (Ciba Speciality Chemicals), benzotriazol compounds, salicylates, substituted tolyl and metal chelate compounds are suitable, wherein benzotriazol derivatives are preferred. Combinations of the compounds stated above are also possible. The quantities usually used are between 0.1 and 10% by weight. The antioxidants are preferably used in quantities of 0.15 to 0.5% by weight relative to the polymeric polyol component B.

To set certain properties of the polyurethane gel foam, further additives that are customary in the art can be used. These include, for example, colorants such as titanium dioxide, fillers such as talcum, chalk, clay, etc. It is also possible to include certain hydrophilic polymers, for example, PVOH (polyvinyl alcohol), polyvinylpyrrolidone, hydroxylpropyl cellulose, polyvinyl methyl ether and cellulose ester, especially its acetates with a low degree of substitution. These can increase the wettability of the polyurethane gel foam. The fillers are understood to be the fillers usually used in polyurethane chemistry. These include zink oxide, titanium oxide and silicic acid derivatives (e.g. Aerosile® (Degussa)). Further possible additives are, for example, the organically or inorganically based short fibers (e.g. textile fibers).

To increase the wetting of the substrate, usual wetting agents can be added to the polyurethane gel foam: for example, poloxamers (copolymers of polyoxyethylenes and polyoxypropylenes), sorbitan esters, fatty acids such as Span® (Sigma-Aldrich), esters of polyoxyethylene sorbitan and fatty acids, such as polysorbates or Polysorbate® (Spectrum Chemical), polyoxyethylated hydrated castor oils such as Cremophor® (BASF), polyoxyethylene stearates, e.g. Myrj® (Uniqema) or any combination of these wetting agents. A polysorbate is preferably used as the wetting agent.

The polyurethane gel foam can additionally contain tackifier resins. Natural, modified natural, or synthetic resins can be used, typically with mean number-average molar masses up to 1500 g/mol. The compatibility of the resins with the further components must be checked in routine tests that are customary in the art. For example, carbohydrate resins are suitable, in particular, C5 to C9 resins, preferably with C5 resins, modified C9 resins, and similar. All carbohydrate resins can be partially or fully hydrated. Natural resins such as balsamic resin or colophony can also be used. These resins can also be esterified with appropriate polyfunctional alcohols such as pentaerythritol ester, glycerine ester, diethylene glycol ester, triethylene glycol ester or methyl ester and be used in this condition. Known commercial products are, for example, "Staybelite" ester 10, "Foral" 85-105, "Hercolyn" D, "Alresen" 214 R, "Alresen" 191 R, "Alresen" 500 R 80 and "Cellolyn" 21 s. Polyterpene resins such as terpene phenol resin can also be included as tackifier resins, as can the synthetic resins: ketone, coumarone and indene resins. Carbohydrate resins are also possible, for example, those having commercial names such as "Ketonharz" N, "Lutonal" J 30, "Lutonal" J 60, "Vinnapas" B 17, "Vinnapas" 50 V 1, carbohydrate resin 95 KW 10, KW 20 and KW 30. Polyvinyl ether is also an effective tackifier. Acrylate resins can also be used alone or in mixtures with the tackifiers stated above.

According to an especially preferred embodiment, the invention concerns, in particular, a polyurethane gel foam and a wound dressing comprising a polyurethane gel foam, in particular, as a wound contact layer, wherein the polyurethane gel foam is obtained from the following components:
 a) an isocyanate component A having a functionality f of $f_A \leq 3$,
 b) a polymeric polyol component B having a functionality f of $f_B \leq 6$,
 c) a polysaccharide C, comprising at least one uronic acid or a salt thereof, and
 d) auxiliary and additional substances wherein the ratio of the number of isocyanate groups of the isocyanate component A to the total number of hydroxyl groups, carboxy groups and carboxylate groups in the polymeric polyol component B and in the polysaccharide C corresponds to the ratio 1:2 to 1:30, the auxiliary and additional substances being selected from the group of catalysts, stabilizers and antioxidants. In particular, a Bi(III)-carboxylate catalyst and vitamin E are used as auxiliary and additional substances.

Polyurethane gel foams obtained in this way can also exhibit pressure-sensitive adhesive properties. According to a further embodiment, this invention also concerns, in particular, a pressure-sensitive adhesive polyurethane gel foam and a wound dressing that comprises a pressure-sensitive adhesive polyurethane gel foam, in particular, as a wound contact layer.

The adhesive polyurethane gel foam is a gel foam that exhibits weak to moderate pressure-sensitive adhesion to human skin or tissue. In particular, an inventive wound dressing has an adhesive force of 0.05 to 5 N/25 mm, in particular, of 0.05 to 3 N/25 mm and highly preferably of 0.05 to 2 N/25 mm. The adhesive force according to Test 1 (cf. test methods) is measured against steel with a pull-off angle of 90°.

The wound contact layer according to this invention is understood to be a layer that has a first and a second side, wherein the first side forms direct contact with the wound in the ready-to-apply condition of the wound dressing. There are no restrictions on the shape and dimensions of the wound contact layer. With respect to the absorbent layer, this wound contact layer can cover the full surface or be discontinuous and/or have an even or a profiled layer thickness and/or a regular or irregular pattern.

According to this invention, the wound contact layer should be connected to the absorbent layer. This means that the wound contact layer is in direct contact in at least one region of its second side with a first side of the absorbent layer that faces the wound in the ready-to-apply state. The wound dressing especially preferably comprises a wound contact layer whose second side is connected to the first side of the absorbent layer over its full surface. As an alternative to this, the wound contact layer can also be integrally connected to the absorbent layer. This means that the two interconnected and adjacent layers form an inseparable transition layer at their bordering surfaces. With these integrally connected layers, a laminate is also provided that does not comprise separable layers that are interconnected chemically and/or physically.

Accordingly, this invention also concerns a multiple-layer wound dressing comprising a carrier layer, an absorbent layer with a first and a second side and a wound contact layer with a first and a second side, wherein the second side of the wound contact layer is connected to the first side of the absorbent layer over its full surface and comprises a polyurethane gel foam. This wound dressing especially preferably has a wound contact layer that covers the full surface with respect to the first side of the absorbent layer. This wound dressing highly preferably has a wound contact layer that is integrally connected to the absorbent layer and that, in particular, covers the full surface with respect to the first side of the absorbent layer.

Finally, the wound dressing can have a wound contact layer that does not cover the full surface with respect to the first side of the absorbent layer, but omits individual regions of the absorbent layer, for example, to attach an adhesive application to fix the wound dressing to the skin of a patient. Alternatively, the wound dressing can be constituted not to cover the full surface with respect to the absorbent layer by choosing a discontinuous wound contact layer that provides regularly or irregularly disposed omitted regions. These omitted regions allow for improved passage of wound exudates from the wound to the absorbent layer.

Wound dressings having a wound contact layer whose layer thickness is less than 1000 μm have proven especially advantageous embodiments. In particular, an inventive wound dressing therefore has a wound contact layer with a layer thickness of 10 to 1000 μm, in particular, of 10 to 500 μm and highly preferably of 10 to 250 μm. Wound dressings with such layer thicknesses exhibit no wound adhesion as well as the ability to accept wound exudate exuded from a wound and to pass it on to the absorbent layer. These layer thicknesses can be equal at every position of the wound contact layer or have different values in different regions of the wound contact layer.

Any material that is currently normally used as an absorbent layer in modern wound treatment can be deployed as the absorbent layer. These include, in particular, materials that can be applied in moist wound therapy. However, absorbent layers are highly preferred that both take up wound exudates, thus acting as an absorbent, and give off moisture to the wound. Absorbent layers are also preferred that are transparent or translucent. According to an especially preferred embodiment of this invention, the absorbent layer of the wound dressing comprises a hydrophilic polymer foam, an absorbent nonwoven, a polymer matrix comprising at least one hydrocolloid, a freeze-dried foam or combinations thereof.

If a hydrophilic polymer foam is used as the absorbent layer, it has been shown that the wound dressing is especially well adapted to the wound to be treated. In particular, hydrophilic polyurethane foams are suitable as polymer foams. Accordingly, an especially preferred wound dressing comprises an absorbent layer made of a hydrophilic polyurethane foam. These polyurethane foams have a free absorption of at least 10 g/g, in particular, at least 12 g/g and highly preferably at least 15 g/g, wherein the free absorption is determined according to DIN EN 13726-1 (2002). Further, these foams have an average cell size of less than 1000 μm, in particular, 200 to 1000 μm and highly preferably 200 to 700 μm. The cell size on a first surface of the absorbent layer can have a different value from the cell size of a second surface of the absorbent layer. Furthermore, preferred hydrophilic polyurethane foams have a density of less than 150 kg/m³, in particular, less than 140 kg/m³ and highly preferably 70 to 120 kg/m³.

In an inventive alternative, the absorbent layer preferably comprises non-water-soluble cellulose fibers, in particular, largely delignified technical cellulose fibers, in particular, wood cellulose fibers, in particular with a fiber length shorter than 5 mm. The fiber material can also contain hydrophilic fiber material made from regenerated cellulose, carboxymethyl cellulose, carboxyethyl cellulose, hydroxymethyl cellulose or hydroxyethyl cellulose. A fiber mixture of cellulose, regenerated cellulose, carboxymethyl cellulose, carboxyethyl cellulose, hydroxymethyl cellulose, or hydroxyethyl cellulose fibers and fibers of polyethylene, polypropylene, or polyester can also be used. In a highly preferred embodiment, the absorbent layer comprises a mixture of cellulose fibers, polypropylene fibers and particulate super-absorbent polymer, preferably of crosslinked sodium polyacrylate.

Various different materials can be used as the carrier layer. Textile carrier materials, nonwovens, polymer films, or polymer foams are usually used in wound dressings. In particular, polymer films or polymer foams can be used as the carrier layer of an inventive wound dressing. Polymer films that exhibit great permeability to water vapor are highly preferred. Films are especially preferred which are made from polyurethane, polyetherurethane, polyesterurethane, polyether-polyamide-copolymers, polyacrylate, or polymethacrylate. In particular, a polyurethane film, polyesterurethane film or polyetherurethane film is preferred as the polymer film. Polymer films are also highly preferred that have thicknesses of 15 to 50 µm, in particular, 20 to 40 µm, and highly preferably 25 to 30 µm.

The permeability to water vapor of the polymer film of the wound dressing is preferably at least 750 g/m²/24 hours, in particular, at least 1000 g/m²/24 hours and highly preferably at least 2000 g/m²/24 hours (measured according to DIN EN 13726). In especially preferred embodiments, these films have a moisture-tight adhesive edge zone. This edge zone ensures that the wound dressing can be applied and fixed in its intended location and that no liquid can exit between the film and the skin surrounding the surface to be treated. Adhesives are especially preferred that, in a thin application of 20 to 35 g/m² together with the film, have a permeability to water vapor of at least 800 g/m²/24 hours and preferably of at least 1000 g/m²/24 hours (measured according to DIN EN 13726).

In an alternative and especially preferred embodiment of an inventive wound dressing, the carrier layer can be made of a polymer foam. In particular, in this embodiment, the polymer foam is a polyurethane foam. These polyurethane foams are essentially made of closed-cell polyurethane foams and have, in particular, a thickness of 0.01 to 2 mm. Essentially closed-cell polyurethane foams prove especially advantageous because these foams are both permeable to water vapor and form a barrier for dirt and germs. This carrier material especially preferably exhibits a permeability to water vapor of at least 750 g/m²/24 hours, in particular, at least 1000 g/m²/24 hours and highly preferably at least 1200 g/m²/24 hours (measured according to DIN EN 13726).

In a further preferred embodiment, the inventive wound dressing has a laminate made of two different polyurethane foams as a carrier layer and as an absorbent layer. In particular, this wound dressing consists of a laminate made of two different polyurethane foams that is coated with a wound contact layer consisting of a pressure-sensitive adhesive polyurethane gel foam on the side facing the wound in the ready-to-apply condition. Therefore, the invention also concerns a wound dressing comprising a carrier layer consisting of a first hydrophobic polyurethane foam that is permeable to water vapor, an absorbent layer consisting of a hydrophilic, absorbent polyurethane foam and a wound contact layer connected, in particular, integrally connected with the absorbent layer and comprising a pressure-sensitive adhesive polyurethane gel foam that is different from the hydrophilic foam. In particular, this wound dressing also comprises an absorbent layer that has a higher free absorption than the wound contact layer.

This wound dressing is especially advantageously used as a supporting measure in modern wound treatment because, owing to the wound contact layer, no wound adhesion occurs, no maceration of the skin surrounding the wound occurs, the wound exudates exuded from the wound are taken up quickly, and the wound dressing can be fixed to the skin surrounding the wound.

In an alternative form of an inventive wound dressing, a wound contact layer further comprises a means of actively supporting wound healing, in particular, an antimicrobial means, a vitamin or provitamin, a fatty acid or fatty acid ester or a means of actively promoting tissue build-up.

According to an especially preferred alternative, the wound contact layer further comprises at least one antimicrobial means. In particular, antimicrobial metals or salts thereof such as silver or salts thereof are suitable. In an especially preferred embodiment, the wound contact layer comprises an antimicrobial means and a carrier material for the antimicrobial means. As the carrier material, a nonwoven or a textile material, such as a knitted or a woven, is preferably used that is coated with a metal with an antimicrobial effect, preferably silver or silver salts. It is especially advantageous if the polyurethane gel foam is anhydrous.

According to a further embodiment, the present invention also concerns, a multiple-layer wound dressing comprising a carrier layer, an absorbent layer, a wound contact layer and a distribution layer, wherein the wound contact layer comprises a polyurethane gel foam. In particular, the absorbent layer is connected to the wound contact layer. Such a wound dressing especially preferably has a distribution layer between the carrier layer and the absorbent layer, which comprises, in particular, a hydrophilic polyurethane foam. The distribution layer enables distribution of the wound exudates taken up over the entire surface of the wound dressing, in particular, above the absorbent layer. The wound exudates are thereby taken up not only in the z-direction (away from the wound toward the carrier layer), but also in the x-y direction (over the surface of the wound dressing).

According to a further aspect, the invention also concerns a method for the production of a polyurethane gel foam, in particular, a method for the production of the polyurethane gel foam described above, in particular, for use as a wound contact layer in a wound dressing. A method for production of a polyurethane gel foam for use as a wound contact layer is thus also the object of this invention and is characterized in that the polyurethane gel foam is obtained from at least the following components, which have been made to react:

a) an isocyanate component A having a functionality f of $f_A \leq 3$, b) a polymeric polyol component B having a functionality f of $f_B \leq 6$, and c) a polysaccharide C, comprising at least one uronic acid or a salt thereof, wherein the ratio of the number of isocyanate groups of the isocyanate component A to the total number of hydroxyl groups, carboxy groups and carboxylate groups in the polymeric polyol component B and in the polysaccharide C corresponds to the ratio 1:2 to 1:30.

According to a further embodiment of the present invention, the ratio of the number of isocyanate groups of the isocyanate component A to the total number of hydroxyl groups, carboxy groups and carboxylate groups in polymeric polyol component B and in polysaccharide C must be 1:3 to 1:30, in particular 1:4 to 1:30, in particular 1:4 to 1:20, and highly preferably 1:5 to 1:20.

It must be emphasized here that both the polymeric polyol component B and polysaccharide C are reactants that react with the isocyanate component A. Polysaccharide C can thereby react with the isocyanate component A by means of the existing hydroxyl groups, thus forming a urethane bond, and also by means of an existing carboxy group of the uronic acid, thus forming an amide bond. This amide bond is formed with simultaneous release of gaseous carbon dioxide, wherein the polyurethane gel foam is produced without introducing additional gases.

In particular, a method for the production of a pressure-sensitive adhesive polyurethane gel foam is the object of this invention.

Irrespective of this, the polyol component B and the polysaccharide C are mixed to form a polyol-polysaccharide dispersion in a first step of the method. In a further preferred embodiment of the method, in a first step of the method, the polyol component B and the polysaccharide C are blended to form a polyol-polysaccharide dispersion and the polyol-polysaccharide dispersion thus produced is made to react with the isocyanate component A in a second step of the method. Further auxiliary and additional substances can be mixed into the polyol-polysaccharide dispersion.

A method for producing the polyurethane gel foam is especially preferred in which the ratio of the number of isocyanate groups of the isocyanate component A to the total number of the carboxy groups and carboxylate groups in the polysaccharide C corresponds to the ratio 1:0.5 to 1:10.

A method for producing a polyurethane gel foam is also preferred in which the isocyanate component A is selected from the group of aliphatic di- or polyisocyanates, alicyclic di- or polyisocyanates or mixtures thereof. Isophorone diisocyanate, an isophorone diisocyanate prepolymer or a mixture thereof is especially preferably used as the isocyanate component A, wherein the isophorone diisocyanate prepolymer is, in particular, obtainable from isophorone diisocyanate and a polyether polyol D with a functionality f of $f_D \leq 3$. A polyether polyol D is highly preferred that is selected from the group of polyethylene glycols, polypropylene glycols, polyethylene polypropylene glycols or mixtures thereof, wherein the polyether polyol D has a mean number-average molar mass $M_n$ of at least $M_n(D)=2000$ g/mol and no more than $M_n(D)=10,000$ g/mol.

Irrespective of this, a substance can be especially preferably used as the polyol component B that has a functionality f of $3 \leq f_B \leq 6$. In particular, a polyether polyol can be used as the polyol component B that further preferably has a functionality f of $3 \leq f_B \leq 6$. A polyether polyol can further preferably be used as a polyol component B that has a mean number-average molar mass $M_n$ of 3000 to 10,000 g/mol.

According to a further embodiment of the invention, a polysaccharide C can be used in the method for producing a polyurethane gel foam that comprises, as the uronic acid, guluronic acid or a salt thereof, mannuronic acid or a salt thereof, galacturonic acid or a salt thereof, glucuronic acid or a salt thereof, iduronic acid or a salt thereof, or mixtures of these uronic acids or salts thereof. In particular, polysaccharides can also be used in the method as the polysaccharide C, which are selected from the group of alginic acid or salts thereof, hyaluronic acid or salts thereof, glucose aminoglycans or salts thereof, the xanthans or salts thereof, or mixtures of these polysaccharides or salts thereof. A method is highly preferred in which the polysaccharide C is a calcium alginate, a sodium alginate, a sodium calcium alginate or mixtures thereof.

In a further embodiment, the invention also concerns a method for manufacturing a wound dressing. In the method, a polyurethane gel foam is produced in a first step by making at least the following components react:
a) an isocyanate component A having a functionality f of $f_A \leq 3$,
b) a polymeric polyol component B having a functionality f of $f_B \leq 6$, and
c) a polysaccharide C, comprising at least one uronic acid or a salt thereof, wherein the ratio of the number of isocyanate groups of the isocyanate component A to the total number of hydroxyl groups, carboxy groups and carboxylate groups in the polymeric polyol component B and in the polysaccharide C corresponds to the ratio 1:2 to 1:30.

In particular, the wound dressing comprises the thus produced polyurethane gel foam as the wound contact layer.

In a second step of the method, the completed polyurethane foam is applied to, laminated onto, or transferred onto a carrier layer or onto an absorbent layer. Herein, the completed polyurethane gel foam is, in particular, applied to, laminated onto, or transferred onto an absorbent layer, wherein an absorbent hydrophilic polymer foam or an absorbent textile material is the absorbent layer.

In a first step of the method for producing the wound dressing, a polyurethane gel foam can be directly formed on a carrier layer or on an absorbent layer, wherein the carrier layer or the absorbent layer is part of the wound dressing. A wound dressing is thereby provided which has an absorbent layer in direct contact with the polyurethane gel foam.

BRIEF DESCRIPTION OF THE DRAWING

The invention is explained below using drawings, which are not intended to restrict the invention in any way. The figures show.

DESCRIPTION OF THE PREFERRED EMBODIMENT

Figure 1:
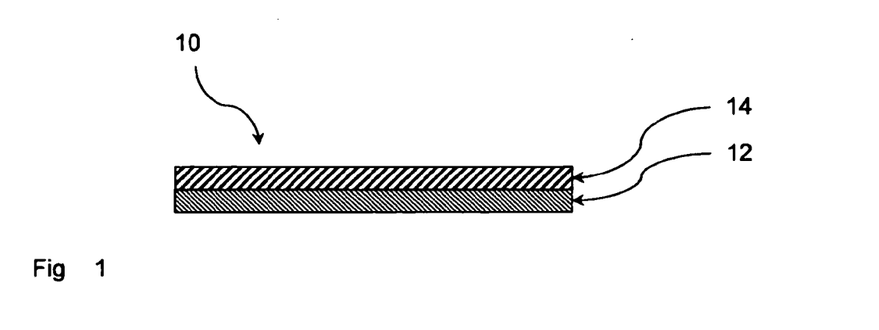
FIGS. 1 to 3 Alternative embodiments of an inventive wound dressing in cross-section.

FIG. 1 shows the simplest structure of an inventive wound dressing (10). The wound dressing consists of a wound contact layer (12) made of an inventive polyurethane gel foam that is applied to an absorbent nonwoven. Coating with the polyurethane gel foam both prevents adhesion to the wound and provides a wound dressing that takes up liquids well and quickly, despite the coating.

Figure 2:
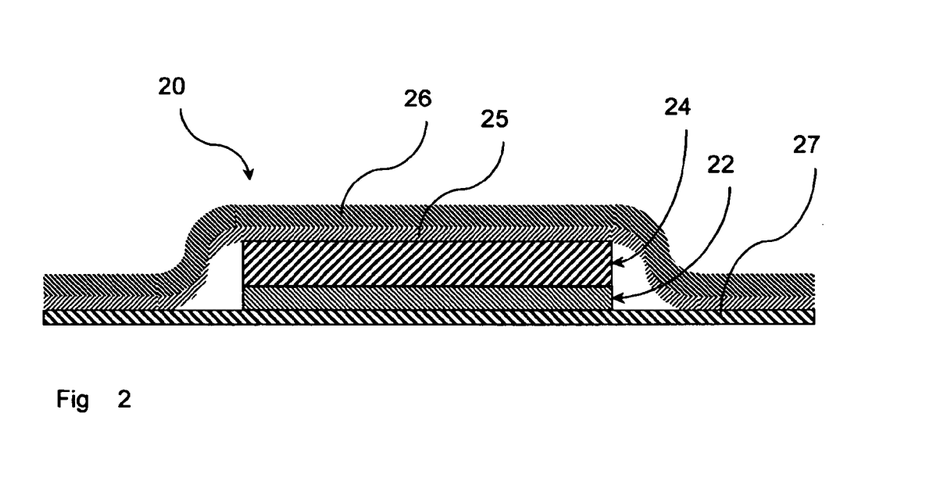

FIG. 2 shows an inventive wound dressing (20) as a so-called island dressing. The wound dressing consists of an absorbent, hydrophilic polyurethane foam as an absorbent layer (24), which is coated on the side facing a wound in the ready-to-apply condition with a wound contact layer (22) made of an inventive pressure-sensitive adhesive polyurethane gel foam over the entire surface. The polyurethane gel foam makes direct contact with the absorbent polyurethane foam. On the side of the absorbent layer facing away from the wound in the ready-to-apply condition, a carrier layer (26) made of closed-cell polyurethane foam is applied using an acrylate pressure-sensitive adhesive (25) over its full surface. Both the wound contact layer (22) and the adhesive edge surrounding the entire wound contact layer are covered by siliconized release paper (27) before the wound dressing is used. This wound dressing has two pressure-sensitive adhesive zones of different adhesive strengths.

Figure 3:
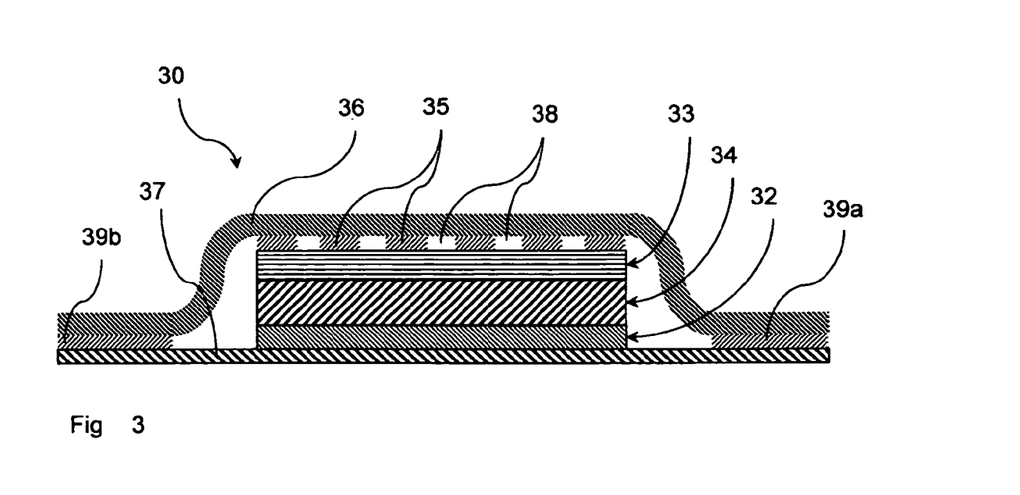

FIG. 3 also shows an inventive wound dressing (30) as an island dressing. The wound dressing comprises a wound contact layer (32) made of an inventive polyurethane gel foam that is applied to a hydrophilic, absorbent polyurethane foam (34) over its full surface and is integrally connected with the foam. The absorbent layer has a layer thickness of 5 mm, wherein the polyurethane foam exhibits a cell size of 300 to 900 μm. A further absorbent layer (33) is applied to the surface of the absorbent layer opposite the wound contact layer between the carrier layer (36) and the absorbent layer (34). This absorbent layer (33) is used as a distribution layer for the quantity of liquid already taken up by the wound contact layer (32) and the absorbent layer (34). The absorbent distribution layer permits even distribution of the liquids taken up in the x-y direction, whereas the absorbent layer (34) and the wound contact layer (32) ensure absorption of the wound exudates in the z-direction, i.e. perpendicular to the wound surface. The carrier layer (36) comprises a thin polyurethane film that is very permeable to water vapor, having a layer thickness of 70 μm. The distribution layer comprises a distribution nonwoven made of cellulose fibers that is attached to the carrier layer (36) by means of the acrylate pressure-sensitive adhesive (35) applied in stripes. In this way, the parts (38) remaining free of acrylate adhesive offer better water vapor exchange with the surroundings than a film coated over its full surface. Both the wound contact layer (32) and the adhesive edge (39a, 39b) surrounding the entire wound contact layer made of an acrylate pressure-sensitive adhesive are covered by siliconized release paper (37) before the wound dressing is used.

At this point it must be emphasized that the characteristics listed here of the alternative or preferred embodiments of the inventions are not restricted to the individual alternatives. In the context of the present invention, it is rather the case that a combination of embodiments or a combination of each individual characteristic of an alternative form with characteristics of another alternative embodiment is equally to be seen as an inventive object.

Embodiments

A) Test Methods:

1) Adhesive Force on Steel (90° Pull-Off Angle) Based on AFERA 5001)—Test 1

The sample to be tested is stored in a standardized climate (23° C., 50-% relative humidity) for 24 h before testing and thereafter 3 samples, each 25 mm in width and 100 mm in length are taken. The test specimen is carefully laminated by hand onto steel plates and without stretching (acc. to DIN EN 1939), wherein the formation of air bubbles is avoided. A commercially available reinforcement adhesive tape that is not elastic (e.g. Tesa 4104) is applied to the non-adhesive upper side of the sample to eliminate stretching of the foam. The test specimen is rolled on in a defined manner with 20 N/cm using a tape applicator D 427/1 from Sondes Place Research Institute, Surrey, England. The steel plate prepared in this way is inserted into the 90° pull-off device of the Z-005 tensile strain machine from Zwick-Roell, Ulm, Germany, and the free end of the reinforcement tape protruding beyond the sample is clamped into the upper clamp. At a constant pull-off rate of 300 mm/min, the force curve that is required to separate the sample from the steel plate is measured. The adhesive force is calculated using a suitable PC program according to DIN 53 539 (method C).

2) Tack—Test 2

Figure 4A:
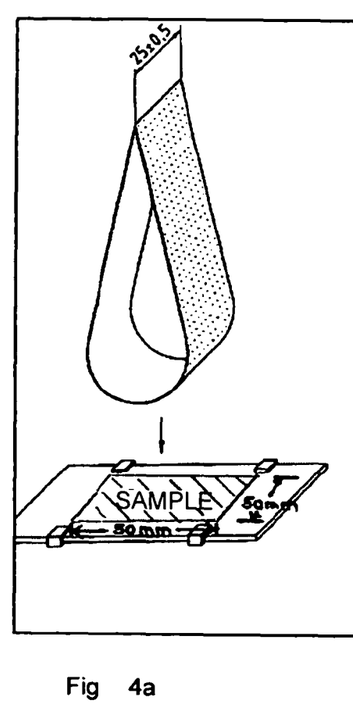
FIGS. 4a and 4b A measurement set-up for determining the tack.
Figure 4B:
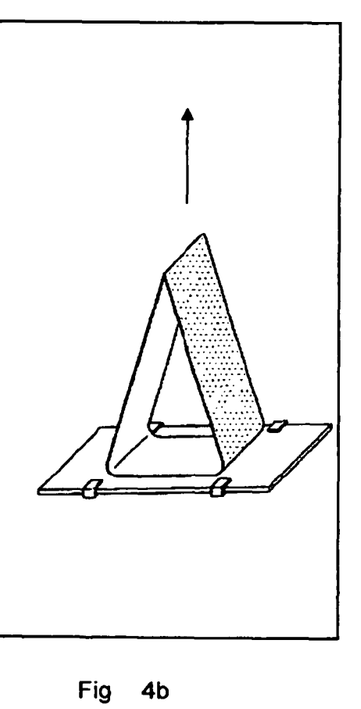

Tack is the term used for the initial stickiness that forms after immediate contact of the surfaces as opposed to the adhesive force that is only fully formed after a contact time. FIG. 4 shows a schematic representation of a measurement set-up for determining the tack. For measurement of the tack, the maximum force is measured that is required to separate a loop of polyester film at a defined rate (300 mm/min) from an adhesive surface with which it was previously put into contact. The sample was stored in a standardized climate (23° C. and 50% relative air humidity) for 24 hours before measurement. A specimen measuring 50×50 mm was attached to the sample plate using double-sided adhesive tape [410B from 3M]. The polyester loop consisting of a 50 μm thick polyester film (Closure-Tape, Gerlinger Industries, Nordlingen, Germany), 175 mm in length and 25 mm in width, was lowered onto the adhesive sample before the beginning of measurement (cf. FIG. 4a). The polyester loop is lowered until the contact surface of the loop on the sample is at least 25×25 mm (cf. FIG. 4b). Measurement is performed immediately after lowering. The measurement measures the maximum force that is required to separate the loop completely from the adhesive wound dressing. For analysis, the Zwick Z005 tensile testing machine [Zwick GmbH & Co. KG, Ulm—Germany] was used.

3) Permeation Rate—Test 3

To perform this test, a blood substitute solution is used, consisting of a mixture of demineralized water (56.4% by weight), glycerine (42.5% by weight, Sigma-Aldrich, Seelze—Germany), high-purity sodium chloride (0.9% by weight, Sigma-Aldrich) and 0.2% by weight of the colorant Allura red (Sigma-Aldrich). The time is determined that the blood substitute solution takes to pass through a polyurethane gel layer with a layer thickness of 180 μm on a polyurethane foam as the absorbent medium. The test is monitored using a commercially available video camera, wherein all the means used must be adjusted for the ambient climate (23° C., 50% rel. air humidity). For this purpose a specimen with a diameter of approx. 5 cm was punched out. On the side of the polyurethane gel foam lying flat and facing upward, 0.5 ml of the blood substitute solution is applied using a pipette. After this, the time is measured that the blood substitute solution requires to penetrate completely through the polyurethane gel foam layer into the polyurethane foam.

B) Inventive Polyurethane Gel Foams

1) Components Used to Manufacture the Polyurethane Gel Foams i) Isocyanate Component A:

To produce inventive polyurethane gel foams, an isophorone diisocyanate prepolymer according to formula (I) is used as the isocyanate component A, where n=0 and m=60±5. The prepolymer has a polypropylene glycol as the spacer group. The prepolymer was produced from isophorone diisocyanate and a polypropylene glycol (polyether polyol D) with a mean number-average molar mass $M_n$ (D)=3500 g/mol. The prepolymer has a low monomer component of isophorone diisocyanate of less than 0.5% by weight.

The prepolymer exhibits the following characteristics:
a) mean number-average molar mass $M_n$: $M_n$ (A)=4000 g/mol
b) functionality f: $f_A$=2
c) mean equivalent mass M(eq): $M(eq)_A$=2000 g/mol
d) number of isocyanate groups per kg (Z): $Z_A$=500 mmol ii) polymeric Polyol Component B As the polymeric polyol component B, a polyethylene polypropylene glycol (polyether polyol) was used that exhibits the following characteristics
a) mean number-average molar mass $M_n$: $M_n$ (B)=6400 g/mol
b) functionality f: $f_B$=4
c) mean equivalent mass M(eq): $M(eq)_B$=1600 g/mol
d) number of isocyanate groups per kg (Z): $Z_B$=625 mmol iii) Polysaccharide C As polysaccharide C, a calcium alginate (Fluka Bio-Chemika No. 21054-Sigma-Aldrich Chemie GmbH Buchs, Switzerland) was used. The polysaccharide is built up from the sugar acids (uronic acids) mannuronic acid and guluronic acid and comprises approx. 510 units of the calcium salt of the disaccharide (guluronic acid-mannuronic acid-$C_{12}H_{16}O_{12}Ca$) per mol. The alginate exhibits the following characteristics:
a) mean number-average molar mass M: $M_n$ (C)=200,000 g/mol
b) mean equivalent mass M(eq)
(relative to hydroxyl groups and carboxy/carboxylate groups): $M(eq)_{C1}$=19.43 g/mol
c) mean equivalent mass M(eq)
(relative to carboxy/carboxylate groups): $M(eq)_{c2}$=196.08 g/mol iv) Further Auxiliary and Additional Substances As further auxiliary and additional substances, bi(III)-neodecanoate (Coscat 83°—Vertellus Performance Materials Inc., Greensboro, N.C., U.S.A.) and vitamin E (tocopherol—Merck KGaA, Darmstadt, Germany) were used.

The components A and B can be ordered from Nolax AG (Sempach Station—Switzerland) by the name M 41.3032, wherein the polymeric polyol component B comprises the further auxiliary and additional substances stabilizer and catalyst.

2) Composition and Production of the Polyurethane Foams and Wound Dressings Produced from them The polyurethane gel foams have the compositions reproduced in Table 1.

TABLE 2

Equivalents used

| | Number of NCO groups in the isocyanate A [mmol] | Number of OH groups in the polyol B [mmol] | Number of OH groups and COOH/COO$^\ominus$ groups in the alginate [mmol] | Number of COOH/COO$^\ominus$ groups in the alginate [mmol] |
|---|---|---|---|---|
| PUALGS1 | 5.29 | 7.83 | 19.43 | 6.48 |
| PUALGS2 | 4.41 | 6.72 | 16.68 | 5.56 |
| PUALGS3 | 5.05 | 6.85 | 33.97 | 11.32 |
| PUALGS4 | 4.49 | 6.13 | 30.29 | 10.10 |
| PUALGS5 | 4.49 | 5.69 | 42.07 | 14.02 |
| PUALGS6 | 5.14 | 6.65 | 49.11 | 16.37 |
| PUALGS7 | 5.58 | 6.65 | 62.73 | 20.91 |
| PUALGS8 | 5.77 | 4.77 | 118.12 | 39.37 |

TABLE 3

Ratios used

| | Ratio of NCO groups to OH groups (in the polyol B) | Ratio of NCO groups to OH groups and COOH/COO$^\ominus$ groups (in the alginate and polyol B) | Ratio of OH groups (in the polyol B) to OH groups and COOH/COO$^\ominus$ groups (in the alginate) | Ratio of NCO groups to COOH/COO$^\ominus$ groups (in the alginate) |
|---|---|---|---|---|
| PUALGS1 | 1:1.48 | 1:5.15 | 1:2.48 | 1:1.22 |
| PUALGS2 | 1:1.52 | 1:5.30 | 1:2.48 | 1:1.26 |
| PUALGS3 | 1:1.36 | 1:8.09 | 1:4.96 | 1:2.24 |
| PUALGS4 | 1:1.37 | 1:8.12 | 1:4.95 | 1:2.25 |
| PUALGS5 | 1:1.27 | 1:10.64 | 1:7.40 | 1:3.12 |
| PUALGS6 | 1:1.30 | 1:10.86 | 1:7.38 | 1:3.19 |
| PUALGS7 | 1:1.19 | 1:12.43 | 1:9.44 | 1:3.75 |
| PUALGS8 | 1:0.83 | 1:21.30 | 1:24.76 | 1:6.82 |

The individual components caused to react have the equivalents shown in Table 2. For example, the polyol used in the composition PUALGS1 has 7.83 mmol of hydroxyl groups (12.533 g*1000 mmol)/1600 g=7.83 mmol) (cf. Table 2—Equivalents used). This corresponds to the number of hydroxyl groups in the polyol used (with reference to the mass of polyol used). This quantity of hydroxyl groups has been made to react with 5.29 mmol of isocyanate groups from the isophorone diisocyanate prepolymer and 19.43 mmol of hydroxyl groups and carboxy or carboxylate groups from the

TABLE 1

Composition of the polyurethane gel foams

| | Isocyanate A | | Polyol B | | Polysaccharide C | | Stabilizer | | Catalyst | |
|---|---|---|---|---|---|---|---|---|---|---|
| | [g] | % by weight | [g] | % by weight | [g] | % by weight | [g] | % by weight | [g] | % by weight |
| PUALGS1 | 10.58 | 43.25 | 12.533 | 51.24 | 1.27 | 5.19 | 0.025 | 0.10 | 0.052 | 0.21 |
| PUALGS2 | 8.82 | 42.57 | 10.744 | 51.85 | 1.09 | 5.26 | 0.022 | 0.11 | 0.044 | 0.21 |
| PUALGS3 | 10.09 | 43.25 | 10.955 | 46.96 | 2.22 | 9.52 | 0.020 | 0.09 | 0.045 | 0.19 |
| PUALGS4 | 8.97 | 43.10 | 9.800 | 47.09 | 1.98 | 9.51 | 0.020 | 0.10 | 0.040 | 0.19 |
| PUALGS5 | 8.98 | 43.01 | 9.100 | 43.58 | 2.75 | 13.17 | 0.012 | 0.06 | 0.038 | 0.18 |
| PUALGS6 | 10.27 | 42.46 | 10.645 | 44.01 | 3.21 | 13.27 | 0.021 | 0.09 | 0.044 | 0.18 |
| PUALGS7 | 11.16 | 42.99 | 10.635 | 40.97 | 4.10 | 15.79 | 0.021 | 0.08 | 0.044 | 0.17 |
| PUALGS8 | 11.54 | 42.84 | 7.633 | 28.33 | 7.72 | 28.66 | 0.015 | 0.06 | 0.032 | 0.12 | alginate, wherein the equivalent used is determined in an analog fashion. The ratios shown in Table 3 are set therein. For example, in the composition PUALGS1, the ratio of the number of isocyanate groups used (NCO groups) to the number of reactive groups used from the polyol B (OH groups) and the alginate (OH groups and COOH/COO$^\ominus$ groups) is 1:5.15 (5.29:(19.43+7.83)). The inventive polyurethane gel foam can thus be termed an undercrosslinked polyurethane gel foam.

To manufacture the polyurethane gel foams, a polyol polysaccharide dispersion was initially produced, in this case, a polyol-alginate dispersion. For this purpose, the polyol component B with the auxiliary and additional substances was prepared in the desired quantity in a plastic vessel and the alginate was added in the stated quantity. Both substances were mixed in an open agitator for 15 min at 450 rpm. In a second step, this polyol-alginate dispersion was added to the isocyanate component. For this purpose, precisely 0.01 g of the isocyanate component (component A) was weighed out on a top-bowl balance in a plastic vessel. The polyol-alginate dispersion was then weighed out in the same vessel. This mixture was blended for 45 sec. using a laboratory agitator. After the blending operation, the mass was poured onto silicone paper [Separacon 9120-64 white, Soell Maria GmbH, Nidda-Eichesldorf—Germany] and spread using a squeegee and an Erichsen 335 film applicator [Erichsen GmbH u. Co. KG., Hemer—Germany] in 180 μm layer thickness. Directly thereafter, a hydrophilic absorbent polyurethane foam [Rynel L00562 E, Rynel Inc., Wiscasset, Me., U.S.A. laminated with Scapa 4005 Dry PU Foam, Scapa Medical, Luton, UK] was applied to the hydrophilic side and rolled on with a hand roller. The sample was then activated for 2 minutes in a drying cabinet [FDL115, Binder, Tuttlingen, Germany] at 105° C. After the activation step, the produced laminate was stored for 72 hours at room temperature. Wound dressings were punched out of the laminate produced in this way. The wound dressings have the structure shown in FIG. 2 with the difference that the wound dressings are not manufactured as island dressings and do not have any additional adhesive edge. Table 4 shows some characteristics of these wound dressings.

Here, it must be emphasized that all polyurethane gel foams used have excellent characteristics as a wound contact layer. For example, a wound contact layer is provided that has good to very good pressure-sensitive properties and which also exhibits an especially fast permeation rate for wound exudate.

TABLE 4

Properties of the wound dressings

| Polyurethane gel foams used | Adhesive force on steel (test 1) mean value [N/25 mm] | Tack (test 2) max. force [N/25 mm] | Permeation rate (test 3) [s] |
|---|---|---|---|
| PU gel* | | | 110 |
| PUALGS1 | 1.83 ± 0.38 | 2.00 ± 0.38 | 23 |
| PUALGS2 | | | |
| PUALGS3 | 1.38 ± 0.50 | 1.39 ± 0.28 | 30 |
| PUALGS4 | | | |
| PUALGS5 | 1.57 ± 0.71 | 1.22 ± 0.43 | 20 |
| PUALGS6 | | | |
| PUALGS7 | 1.02 ± 0.13 | 1.12 ± 0.38 | 21 |
| PUALGS8 | 0.61 ± 0.01 | 0.87 ± 0.22 | 26 |

*non-claim-conformant example with the same structure, wherein however as the wound contact layer a hydrophilic polyurethane-elastomer 1 was used without a polysaccharide component acc. to EP 1923077 A1.

The polyurethane gel foams described above were applied to a transparent polyurethane film for examination of the foam structure (PU film VP 940-2, Collano Xiro, Buxtehude, Germany). Production was performed according to the method described above, wherein a slice thickness of 180 μm was again set.

Figure 5:
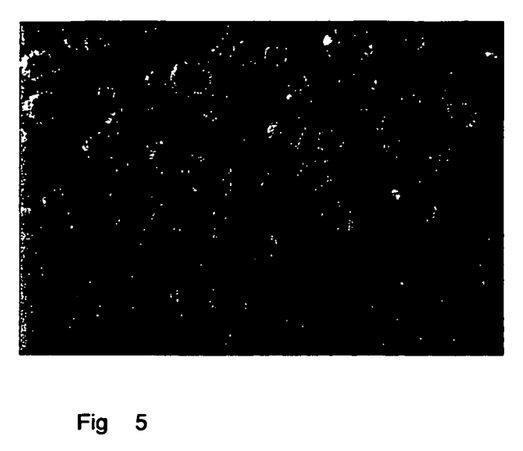
FIGS. 5 and 6 Two light-microscope photographs of an inventive polyurethane gel foam.

FIG. 5 shows a light-microscope photograph of a polyurethane gel foam PUALGS4 with a 9.5% by weight alginate component on a polyurethane film (PU film VP 940-2, Collano Xiro, Buxtehude, Germany) enlarged 30-fold. A closed-cell foam structure can clearly be seen. The polyurethane gel foam is a transparent, homogenous polymer matrix. No alginate particles can be seen in the polymer matrix.

Figure 6:
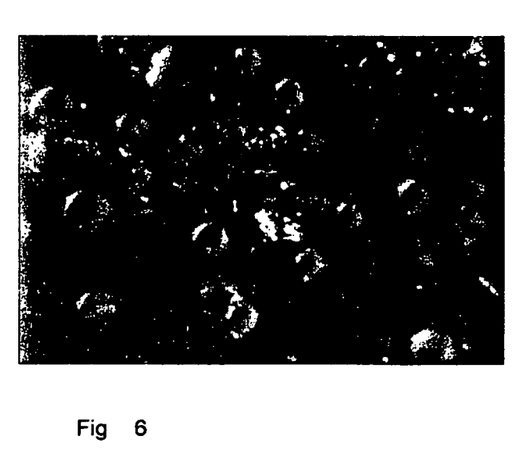

FIG. 6 shows a light-microscope photograph of a polyurethane gel foam PUALGS6 with a 13.2% by weight alginate component on a polyurethane film (PU film VP 940-2, Collano Xiro, Buxtehude, Germany) enlarged 30-fold. This polyurethane gel foam has an alginate component that is approx. 4% by weight greater than the polyurethane foam shown in FIG. 5. The higher the alginate component, the less regular the foam structure will appear under the light microscope.

We claim:

1. A polyurethane gel foam for use as a wound contact layer, the polyurethane gel foam being obtained from at least the following components that have been made to react:

an isocyanate component A having a functionality f of $f_A$ ≤3, wherein said isocyanate component A is an isophorone diisocyanate prepolymer;

a polymeric polyol component B, wherein said polymeric polyol component B is a polyether polyol having a functionality f of 4≤$f_B$ ≤5; and a polysaccharide C, wherein said polysaccharide C is calcium alginate, a ratio of a number of isocyanate groups of said isocyanate component A to a total number of hydroxyl groups, carboxy groups and carboxylate groups in said polymeric polyol component B and in said polysaccharide C being less than 1:3 and greater than or equal to 1:30, wherein a ratio of said number of isocyanate groups of said isocyanate component A to said total number of said carboxy groups and said carboxylate groups in said polysaccharide C is 1:3 to 1:10, wherein a ratio of a number of isocyanate groups of said isocyanate component A to a total number of hydroxyl groups, carboxy groups and carboxylate groups in said polymeric polyol component B and in said polysaccharide C is always less than a ratio of said number of isocyanate groups of said isocyanate component A to said total number of said carboxy groups and said carboxylate groups in said polysaccharide C.

2. The polyurethane gel foam of claim 1, wherein the polyurethane foam is a pressure-sensitive adhesive polyurethane gel foam.

3. The polyurethane gel foam of claim 1, wherein said isophorone diisocyanate prepolymer is obtainable from isophorone diisocyanate and a polyether polyol D with a functionality f of $f_D$≤3.

4. The polyurethane gel foam of claim 3, wherein said polyether polyol D is selected from the group consisting of polyethylene glycols, polypropylene glycols, polyethylene polypropylene glycols and mixtures thereof, wherein said polyether polyol D has a mean number-average molar mass $M_n$ of at least $M_n$(D)=2000 g/mol and no more than $M_n$(D)=10,000 g/mol.

5. The polyurethane gel foam of claim 1, wherein said polyether polyol has a mean number-average molar mass $M_n$ of 3000 to 10,000 g/mol.

6. A wound dressing comprising the polyurethane gel foam of claim 1, functioning as a wound contact layer.

7. A wound dressing of claim 6, wherein the wound dressing further comprises an absorbent layer having an absorbent hydrophilic polymer foam or an absorbent textile material.

8. The wound dressing of claim 6, wherein the wound dressing further comprises an absorbent layer in direct contact with the polyurethane gel foam.

* * * * *